United States Patent
Liu et al.

(10) Patent No.: US 11,389,797 B2
(45) Date of Patent: Jul. 19, 2022

(54) METHODS AND SYSTEMS FOR CIRCULATING TUMOR CELL CAPTURE

(71) Applicant: Lian Liu, Tarzana, CA (US)

(72) Inventors: Lian Liu, Tarzana, CA (US); Shuang Hou, Westlake Village, CA (US); Chun-Hao Luo, Agoura Hills, CA (US)

(73) Assignee: Lian Liu, Tarzana, CA (US)

(*) Notice: Subject to any disclaimer, the term of this patent is extended or adjusted under 35 U.S.C. 154(b) by 356 days.

(21) Appl. No.: 16/282,583

(22) Filed: Feb. 22, 2019

(65) Prior Publication Data
US 2020/0009563 A1 Jan. 9, 2020

Related U.S. Application Data

(60) Provisional application No. 62/694,941, filed on Jul. 6, 2018, provisional application No. 62/694,944, filed on Jul. 6, 2018, provisional application No. 62/694,945, filed on Jul. 6, 2018.

(51) Int. Cl.
*B01L 3/00* (2006.01)
*A61B 5/15* (2006.01)
*C12N 5/09* (2010.01)
*G01N 33/50* (2006.01)

(52) U.S. Cl.
CPC ...... *B01L 3/502761* (2013.01); *A61B 5/1405* (2013.01); *C12N 5/0693* (2013.01); *G01N 33/5094* (2013.01); *B01L 2200/0668* (2013.01); *B01L 2300/088* (2013.01); *B01L 2300/0822* (2013.01); *B01L 2300/0848* (2013.01);
(Continued)

(58) Field of Classification Search
CPC ....... B01L 3/502761; B01L 2300/0874; B01L 2300/12; B01L 2200/0668; B01L 2300/088; B01L 2300/0864; B01L 2300/0848; B01L 2300/0822; B01L 3/502707; G01N 33/5094; G01N 33/5436; C12N 5/0693; A61B 5/1405; C12M 25/06
USPC ............... 422/502, 503, 527; 435/7.5, 288.3, 435/288.5; 436/527

See application file for complete search history.

(56) References Cited

U.S. PATENT DOCUMENTS

| 8,186,913 | B2 * | 5/2012 | Toner ..................... C12M 23/16 406/92 |
| 8,304,230 | B2 | 11/2012 | Toner et al. |
| 8,784,012 | B2 | 7/2014 | Toner et al. |

(Continued)

FOREIGN PATENT DOCUMENTS

WO WO-2015153816 A2 * 10/2015 ....... G01N 33/54366

OTHER PUBLICATIONS

Walper et al, "Comparison of single domain antibody immobilization strategies evaluated by surface plasmon resonance", Journal of Immunological Methods, 388 (2013), 68-77 (Year: 2013).*

(Continued)

*Primary Examiner* — Christopher L Chin (57) ABSTRACT

Methods and systems are provided for isolating circulating tumor cells from a peripheral blood supply in order to diagnose early stage cancer and/or evaluate tumor status. In one example, a system for capturing circulating tumor cells includes a substrate having a cell-capturing region, the cell-capturing region having a curved, switchback-like shape and including an array of micropillar structures within the curved, switchback-like shape.

11 Claims, 9 Drawing Sheets

(52) U.S. Cl.
CPC .............. *B01L 2300/0864* (2013.01); *B01L 2300/0874* (2013.01); *B01L 2300/12* (2013.01)

(56) References Cited

U.S. PATENT DOCUMENTS

| | | | |
|---|---|---|---|
| 9,034,658 B2* | 5/2015 | Barber | G01N 33/56972 |
| | | | 436/518 |
| 10,688,492 B2* | 6/2020 | Liu | A61B 5/1405 |
| 10,786,813 B2* | 9/2020 | Liu | G01N 33/5436 |
| 2003/0148401 A1 | 8/2003 | Agrawal et al. | |
| 2005/0273995 A1 | 12/2005 | Kanagasabapathi et al. | |
| 2009/0018033 A1 | 1/2009 | Morgan et al. | |
| 2011/0160869 A1 | 6/2011 | Duch et al. | |
| 2013/0330246 A1* | 12/2013 | Stemmet | B01F 15/065 |
| | | | 422/503 |
| 2014/0315213 A1 | 10/2014 | Nagrath et al. | |
| 2015/0368599 A1 | 12/2015 | Maher et al. | |
| 2016/0123857 A1 | 5/2016 | Kapur et al. | |
| 2016/0202123 A1 | 7/2016 | Jung et al. | |
| 2016/0214107 A1 | 7/2016 | Viasnoff et al. | |
| 2017/0038285 A1 | 2/2017 | Zheng et al. | |
| 2018/0066299 A1 | 3/2018 | Kim et al. | |
| 2019/0097257 A1 | 3/2019 | Dutta | |

OTHER PUBLICATIONS

Li et al ("Binding of Streptavidin to Surface-attached Biotin with Different Spacer Thicknesses", Journal of Wuhan University of Technology—Mater. Sci. Ed., vol. 30, No. 6, Dec. 2015, 1304-1309) (Year: 2015).*

* cited by examiner

METHODS AND SYSTEMS FOR CIRCULATING TUMOR CELL CAPTURE

CROSS REFERENCE TO RELATED APPLICATIONS

The present application claims priority to 1) U.S. Provisional Patent Application Ser. No. 62/594,941, entitled "A Method and Device for CTC Capture and Characterization", filed on Jul. 6, 2018, 2) U.S. Provisional Patent Application Ser. No. 62/694,944, entitled "Non-Invasive Prenatal Test on Single Fetal Cells Isolated from Blood of Pregnant Women", filed on Jul. 6, 2018, 3) U.S. Provisional Patent Application Ser. No. 62/694,945, entitled "Simple and Eco-Friendly Fabrication of Biocompatible Micropillar Array Substrate (MAS) Using Micro-Imprinting", filed on Jul. 6, 2018. The entire contents of the above-identified applications are incorporated herein by reference for all purposes.

This application has subject matter in common with: 1) U.S. Nonprovisional patent application Ser. No. 16/224,576, filed Dec. 18, 2018, for "Methods and Systems from Cell-Based Non-Invasive Prenatal Testing", 2) U.S. Nonprovisional patent application Ser. No. 16/282,640, filed Dec. 18, 2018, for "Biocompatible Micropillar Array Substrate And Methods for Fabricating Such Substrate", the entire disclosures of which are incorporated herein by reference.

FIELD

The present description relates generally to capturing target cells, and more specifically to capturing circulating tumor cells using a microfluidic chip.

BACKGROUND

Metastasis of a tumor in a patient is believed to be caused by circulating tumor cells (CTCs). Circulating tumor cells are shed from the primary tumor into the circulatory system, and travel to different organs, where the CTCs may form a colony as the new tumor site of cancer metastasis. Beside the conventional tissue based diagnostic approaches, including tumor biopsy, PET/CT or MII imaging, CTCs may be detected in a so-called "liquid biopsy" process which is expected to play a more promising role than traditional serum marker detection in peripheral blood of a patient. As a circulating tumor marker, the appearance of CTCs could reflect the existence of a tumor at an early stage. Further, certain tumor specific markers present on CTCs may be used to evaluate cancer therapy efficacy. Additionally, CTC detection in peripheral blood is one of the non-invasive diagnostic methods still offering the possibility for pathological testing and molecular analysis.

SUMMARY

In one embodiment, a system for capturing circulating tumor cells includes a substrate having a cell-capturing region, the cell-capturing region having a curved, switchback-like shape and including an array of micropillar structures within the curved, switchback-like shape.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

The following description relates to systems and methods for capturing circulating tumor cells (CTCs) in a peripheral blood sample. CTCs are cells that are shed from a primary tumor that may travel in the circulatory system, where the CTCs may form colonies at sites distant from the primary tumor (e.g., leading to tumor metastasis). CTCs may be present during the early stages of tumor development. Further, CTCs may express certain markers indicative of the status of the primary tumor. Accordingly, it may be desirable to isolate CTCs as a means to detect tumors at an early stage and/or to monitor tumor status.

However, CTCs exist in the circulatory system with extremely low abundance, comprising as few as one in $10^9$ hematologic cells. Therefore, the challenge for development of CTC isolation and characterization technology is to enrich the CTCs and identify the CTCs while also reducing the background hematologic cells. According to embodiments disclosed herein, CTC cells from blood may be immobilized on a microstructured pathological glass slide incorporated in a microfluidic chip with etched microstructure, which can be used in conjunction with cell picking up technology (such as micromanipulator and laser microdissection) to isolate single CTCs for subsequent molecular analysis. By immobilizing CTCs via the systems and methods described here, the monitoring of patients under medical care, the assessment of drug efficiency, and fundamental oncology research in laboratories may be improved.

As described in more detail below, CTC capture may be carried out by isolating circulating tumor cells from a blood sample by flowing the blood sample through a circulating tumor cell capture microfluidic (CTCCM) chip. The CTCCM chip may be configured to immobilize certain cells, such as circulating tumor cells, and as such may be configured to selectively trap the CTCs while allowing hematologic cells to flow through the chip. The CTCCM chip may include a bottom slide comprised of glass or other suitable material. The bottom slide may be etched to include a plurality of cell-capturing structures. The cell-capturing structures may include a plurality of micropillar structures etched into the glass slide to form an array. The micropillar structures may have a shape that is adapted to preferentially trap target CTCs while allowing blood cells to flow over the cell-capturing structures and out of the CTCCM chip. For example, the micropillar structures may include single circular or conical pillar-like structures packed into an array and each structure may have a diameter of approximately 1 μm, which may assist in trapping CTCs, which are relatively large (e.g., 16 μm in diameter) compared to blood cells (e.g., white blood cells may have a diameter of 6 μm).

The CTCCM chip may further include a corresponding top piece that, when placed on the bottom slide, forms one or more microfluidic channels. The microfluidic channels may be curved in a switch-back manner, which may cause the target CTCs, which are larger than the blood cells, to be retained in the microfluidic channels for a longer time than the smaller blood cells. Together, the curved microfluidic channels and micropillar structures etched on the surface of the bottom slide (and hence on the surface of the microfluidic channels) preferentially immobilize the target CTCs. To further enhance the isolation of target CTCs within a blood sample, the CTCCM chip may be functionalized with antibodies specifically targeting the CTCs of interest. For example, using biotin and streptavidin as linkers, antibodies specific to CTCs may be coupled to the bottom slide of the CTCCM chip.

After the prepared blood sample has been flowed through the CTCCM chip, any immobilized cells may be identified and differentiated from blood cells using immunostaining and/or based on the size of the immobilized cell. Once an immobilized cell has been identified as a possible circulating tumor cell, the circulating tumor cell may be captured via laser dissection or other process for further molecular and/or pathological analysis.

Figure 1:
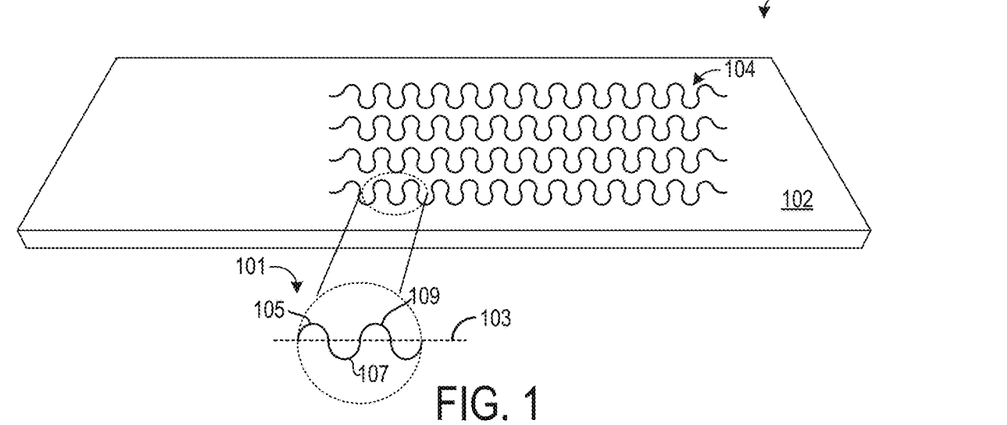
FIG. 1 schematically illustrates an example substrate of a circulating tumor cell capture microfluidic (CTCCM) chip including a plurality of cell-capturing regions.

Turning now to FIG. 1, a bottom slide 100 of a circulating tumor cell capture microfluidic (CTCCM) chip is shown. The bottom slide 100 is comprised of a substrate, such as a glass slide, having a top surface 102. A plurality of cell-capturing regions 104 are formed on the top surface 102 of the substrate. In the example shown in FIG. 1, the plurality of cell-capturing regions each have a curved, switchback-like shape. The plurality of cell-capturing regions will ultimately form the bottom of a plurality of curved microfluidic channels that will be generated once a top piece is added on the bottom slide (which will be explained in more detail below). The plurality of cell-capturing regions may include a first cell-capturing region, a second cell-capturing region, and so forth. As shown, the plurality of cell-capturing regions 104 includes four separate curved, parallel cell-capturing regions, but other numbers of curved cell-capturing regions are possible without departing from the scope of the disclosure. Each cell-capturing region has a curved, switchback-like repeating pattern that extends along a length of the cell-capturing region. Each cell-capturing region has a length that extends along a longitudinal axis of the bottom slide 100. In some examples, the cell-capturing regions may extend along the entirety of the bottom slide, while in other examples (such as the example shown in FIG. 1), the cell-capturing regions may extend along a portion of the bottom slide, such as along a middle region that includes at least 50% of the length of the bottom slide. Further, each micropillar structure array, described in more detail, extends along an entirety of the length and width of a respective cell-capturing region. As shown in more detail in the magnified portion 101, the curved switch-back pattern includes a repeating pattern of a top curved portion fluidly coupled to a bottom curved portion, where the top curved portion and bottom curved portion are reversed relative to each other across a longitudinal axis 103. For example, a first top curved portion 105 extends from a first point on the longitudinal axis to a second point on the longitudinal axis in a shape that constitutes approximately 50% of a circumference of a circle. Likewise, a first bottom curved portion 107 extends from the second point on the longitudinal axis to a third point on the longitudinal axis in a shape that constitutes approximately 50% of a circumference of a circle. A second top curved portion 109 extends from the third point on the longitudinal axis to a fourth point on the longitudinal axis in a shape that constitutes approximately 50% of a circumference of a circle, and so forth. The circular shape of each curved portion may have a diameter of 0.75 mm (outer diameter)/0.25 mm (inner diameter), although other dimensions are possible, such as an outer diameter of 0.7-0.8 mm and an inner diameter of 00.2-0.3 mm.

Figure 2:
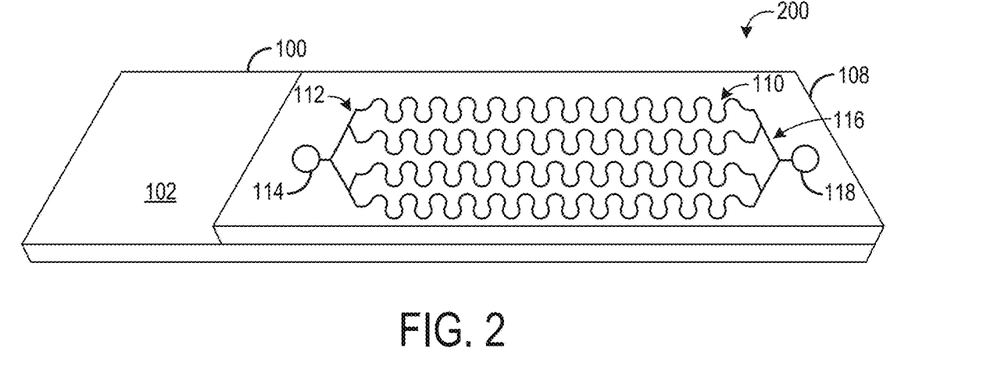
FIG. 2 schematically illustrates an example CTCCM chip.

FIG. 2 shows a schematic diagram of a CTCCM chip 200. CTCCM chip 200 includes the bottom slide 100 described above with respect to FIG. 1, where the bottom slide 100 has a plurality of cell-capturing regions formed on the top surface 102 of the slide 100. CTCCM chip 200 further includes a top piece 108. The top piece 108 may be comprised of a silicone polymer such as polydimethylsiloxane (PDMS) or other suitable polymeric material. The top piece 108 may include a plurality of microfluidic channels printed, carved, or otherwise formed on a bottom surface of the top piece 108 (e.g., a surface facing the top surface 102). Thus, when the top piece 108 is positioned on the top surface 102 as shown in FIG. 2, the bottom surface of the top piece 108 is in face-sharing contact with the top surface 102 of the substrate of the bottom slide and a set of enclosed microfluidic channels 110 is formed. Each enclosed microfluidic channel 110 may be comprised of a respective cell-capturing region on the top surface of the bottom slide and a corresponding microfluidic channel formed on the bottom surface of the top piece 108. The microfluidic channels on the bottom surface of the top piece 108 may be identical in shape to the plurality of cell-capturing regions 104 formed on the top surface 102 of the substrate 102, e.g., a set of curved, switchback-like channels.

In this way, the top surface 102 of the bottom slide may include at least one curved cell-capturing region and the top piece 108 may include at least one curved microfluidic channel. When the top piece 108 is positioned on the top surface 102, a respective curved cell-capturing region may align with a respective curved microfluidic channel to form an enclosed curved microfluidic channel. The enclosed microfluidic channels may have an overall depth of 70 μm and an overall width of 0.5 mm, although other dimensions are possible, such as a depth of 60-80 μm and a width of 0.4-0.6 mm. By providing microfluidic channels having the above dimensions, the flow rate through the channels and/or residence time of the cells through the channels may be such that the target CTCs are preferentially isolated in the channels while the blood cells flow through and out of the channels.

Top piece 108 further includes an inlet 114 coupled to an inlet manifold 112 and an outlet 118 coupled to an outlet manifold 116. The inlet manifold 112 may couple the inlet 114 with the enclosed microfluidic channels 110 (on a first side of the enclosed microfluidic channels) and the outlet manifold 116 may couple the outlet 118 with the enclosed microfluidic channels 110 (on a second side of the enclosed microfluidic channels). In this way, fluid may be supplied to the enclosed microfluidic channels 110 via inlet 114 and inlet manifold 112, and fluid may flow through each of the enclosed microfluidic channels. Fluid that is supplied to inlet 114 may be supplied by a suitable pump, such as a syringe pump, or other fluid supply mechanism. After flowing through the enclosed microfluidic channels, the fluid may be directed to the outlet 118 via the outlet manifold 116. Unlike the bottom slide, the top piece 108 may not include cell-capturing structures or linked antibodies. In this way, when the fluid (e.g., the blood sample) flows through the enclosed microfluidic channels of the CTCCM chip system, the target CTCs may be immobilized on the micropillar structures of the cell-capturing regions. The top piece 108 may then be removed to facilitate immunostaining, laser dissection, etc., of the bottom slide in the region of an immobilized cell.

Figure 3:
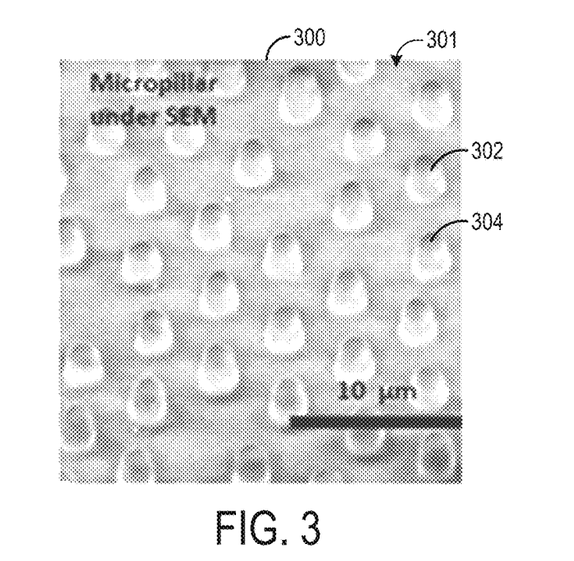
FIG. 3 shows an example image of a micropillar structure array etched on a surface of a substrate of a CTCCM chip at a cell-capturing region.

FIG. 3 shows a first image 300 of a cell-capturing micropillar structure array 301 etched on a surface of a substrate of a CTCCM chip. For example, first image 300 may be an image of a portion of a cell-capturing region of FIG. 1 (it is to be understood that first image 300 is magnified relative to the schematic diagram shown in FIG. 1, such via a scanning electron microscope). The cell-capturing micropillar structure array 301 may include a plurality of micropillar structures, such as pillar 302. Pillar 302 may have a bottom side that is circular is shape and may extend upward from the substrate in a generally cylindrical manner. In some examples, the top side of pillar 302 may be the same diameter as the bottom side. In other examples, the top side may be a smaller diameter. The top side may be curved (as shown) or may be relatively flat. However, other microstructure shapes are possible, such as hexagonal, triangular, rectangular, etc. The pillars may have a diameter of 0.8-1.2 µm, and more specifically 1 µm, which provides strength to pillar structure and prevents the pillar structure from bending over during the fluid flow through the channels, so that the interaction between the pillars and cells is enhanced.

The cell-capturing micropillar structure array etched on the glass slide may include a plurality of micropillar structures spaced apart from one another and distributed equally across the cell-capturing region. For example, pillar 302 may be spaced apart from a second pillar 304 by a suitable amount, such as 3-6 µm from a center of pillar 302 to a center of second pillar 304. The micropillar structures may be distributed in the array in a suitable manner. For example, each pillar may be equally spaced from six other pillars arranged around the pillar in a circular fashion, such that a center of the each pillar is spaced approximately 3-6 µm from the center of each neighboring pillar. However, other array distributions and spacing are possible. By spacing the micropillar structures in the above-described manner, cell capture of the target CTCs may be enhanced.

Thus, a CTCCM chip for use in isolating circulating tumor cells includes two features that may enhance isolation of CTCs from a blood sample, the functional microfluidic chip configuration and the pillar array for efficient cell enrichment. Two strategies for isolating rare cells in a sample include size selecting strategy and micro/nano structure assisted immobilization, which are combined together and realized by the microfluidic channel configuration and structure fabrication on a chip, respectively. First, with the curved microfluidic channel, larger cells (e.g., more than 10 µm in diameter, such as CTCs cells) are trapped selectively with longer retention time during sample flow through the channel, which gives greater chance to increase the contact time of the target cells with the pillar array on the CTCCM chip. Secondly, the pillar structures have a function to immobilize the target cells. The macro structure of 1 µm as the diameter of a pillar blocks the target cell with similar size in the flow and the secondary microstructure enhances the interaction of the cell surface and the substrate. Simultaneously, with the bio-affinity offered after the modification of surface with specific antibodies (described in more detail below), the adhesion of target cells on the substrate may be further enhanced.

Figure 4:
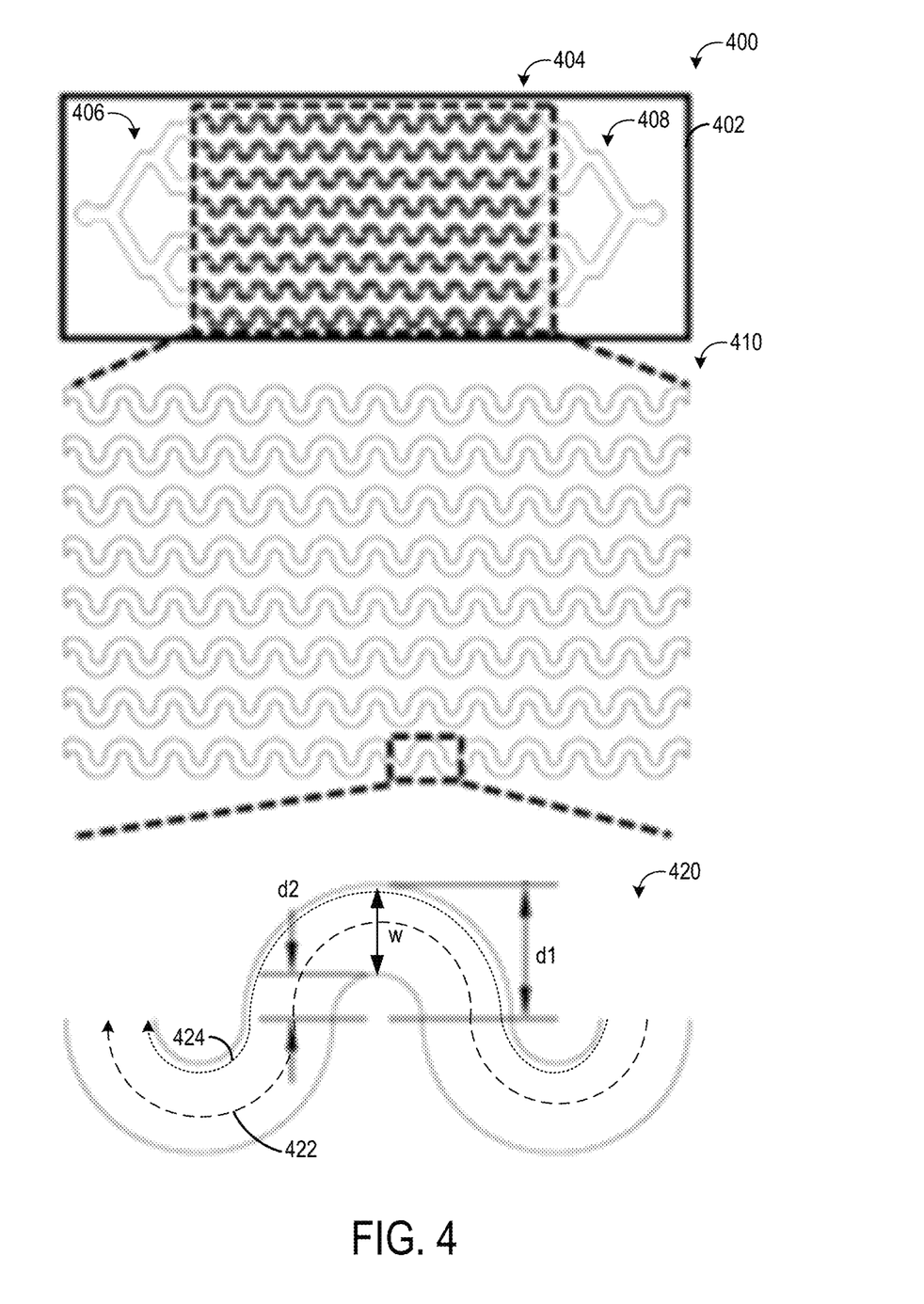
FIG. 4 schematically shows an arrangement of a plurality of curved microfluidic channels of an example CTCCM chip.

FIG. 4 is a schematic 400 of an example top piece 402 that may be placed on a corresponding bottom slide to form a CTCCM chip. As explained above with respect to FIG. 2, top piece 402 may be comprised of PDMS and includes a set of curved microfluidic channels 404. The set of curved microfluidic channels 404 includes eight parallel channels in the example shown in FIG. 4. Each channel of the set of curved microfluidic channels is coupled to an inlet manifold 406 and an outlet manifold 408, as explained above with respect to FIG. 2.

Schematic 400 includes a first magnified view 410 of the set of curved microfluidic channels 404 and a second magnified view 420 of a portion of one of the curved microfluidic channels of the set of curved microfluidic channels 404. As appreciated by the first magnified view 410 and the second magnified view 420, the curved channels each have the same curved shape and are aligned in parallel. Each channel has an outer diameter d1 and an inner diameter d2. In one example, the outer diameter d1 may be 0.75 mm and the inner diameter may be 0.25 mm, though other dimensions are possible. Thus, each channel may have a channel width w of 0.5 mm. The curved microfluidic channels each have a fast-moving region and at least one slow-moving region such that fluid (e.g., a blood sample) flows faster in the fast-moving region than in the slow-moving region. In this way, fluid may flow through the middle of the channel at a different rate than at the sides of the channel due to the curvature of the channel. For example, fluid may through a middle of the channel (such as along dashed line 422) at a first rate (e.g., 0.07 m/min) while fluid may flow along a first side of the channel (such as along dotted line 424) at a second rate (e.g., 0.01 m/min). While not shown in FIG. 4, it is to be understood that top piece 402 is configured to be positioned on a corresponding bottom slide that includes a plurality of cell-capturing regions, as described above. The shape and number of cell-capturing regions may match the shape and number of microfluidic channels. For example, a bottom slide that is configured to be used with top piece 402 may include eight curved, parallel cell-capturing regions.

Figure 5:
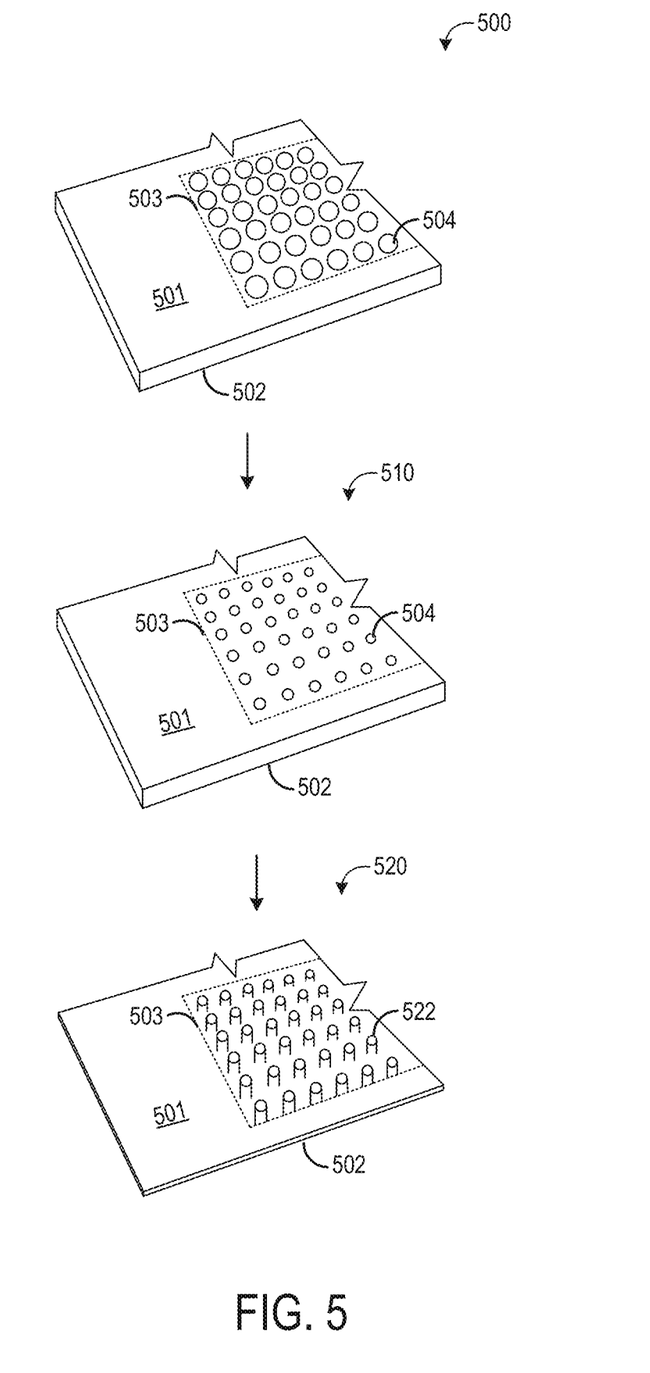
FIG. 5 illustrates an example process for etching a micropillar structure array on a surface of a cell-capturing region of a substrate of a CTCCM chip.

FIG. 5 schematically illustrates a process 500 for producing a cell-capturing micropillar structure array on a bottom slide of a CTCCM chip, such as bottom slide 100 of FIG. 1. As explained above, the bottom slide may be a glass slide 502. The glass slide 502 may have a suitable thickness. The glass slide may be cleaned, such as with piranha solution followed by water and ethanol. Once cleaned, the glass slide is coated with polystyrene beads, such as bead 504. The beads may be added to the glass slide via spincoating or other process. The beads may have an initial diameter, such as 10 µm. The beads may be deposited on the glass slide 502 only within one or more cell-capturing regions. For example, in FIG. 5, the beads are deposited in a cell-capturing region 503 and are not deposited in an outer region 501 surrounding the cell-capturing region 503. It is to be understood that only a portion of glass slide 502 is shown in FIG. 5, and that the glass slide may extend along multiple axes. Likewise, the cell-capturing region 503 may extend beyond the region shown in FIG. 5, and may have a suitable overall shape (e.g., curved).

The size of the polystyrene beads may be decreased via an initial plasma exposure. For example, as shown by the glass slide at 510, the size of the polystyrene beads is decreased (e.g., to 1 μm) upon plasma exposure. A reactive ion etching (RIE) process is then employed to remove the substrate (e.g., the glass slide) between the polystyrene beads. A subsequent application of piranha solution and additional washing (e.g., with water and ethanol) removes the polystyrene beads, leaving an etched slide 520 having micropillar structures, such as pillar 522, that are a suitable height, such as in a range of 0.2-2 μm (e.g., 0.5 μm). As shown in FIG. 5, the entirety of the glass slide 502 is etched, such that the overall height of the glass slide is reduced everywhere other than at the resultant pillars of the cell-capturing region.

In some examples, rather than only depositing the beads in the cell-capturing region(s), the beads may be deposited over all of the top surface of the glass slide, or over all of a middle region of the top surface of the glass slide. Such a configuration may simplify the etching process. However, the presence of pillars over most or all of the top surface may reduce the capacity of the bottom slide to form a tight seal with the top piece, which may compromise the flow of the sample through the enclosed microfluidic channels. Thus, to ensure a tight seal, the surface of the bottom slide at the areas where the top piece will contact the bottom slide may be maintained substantially flat/unpatterned.

Figure 6:
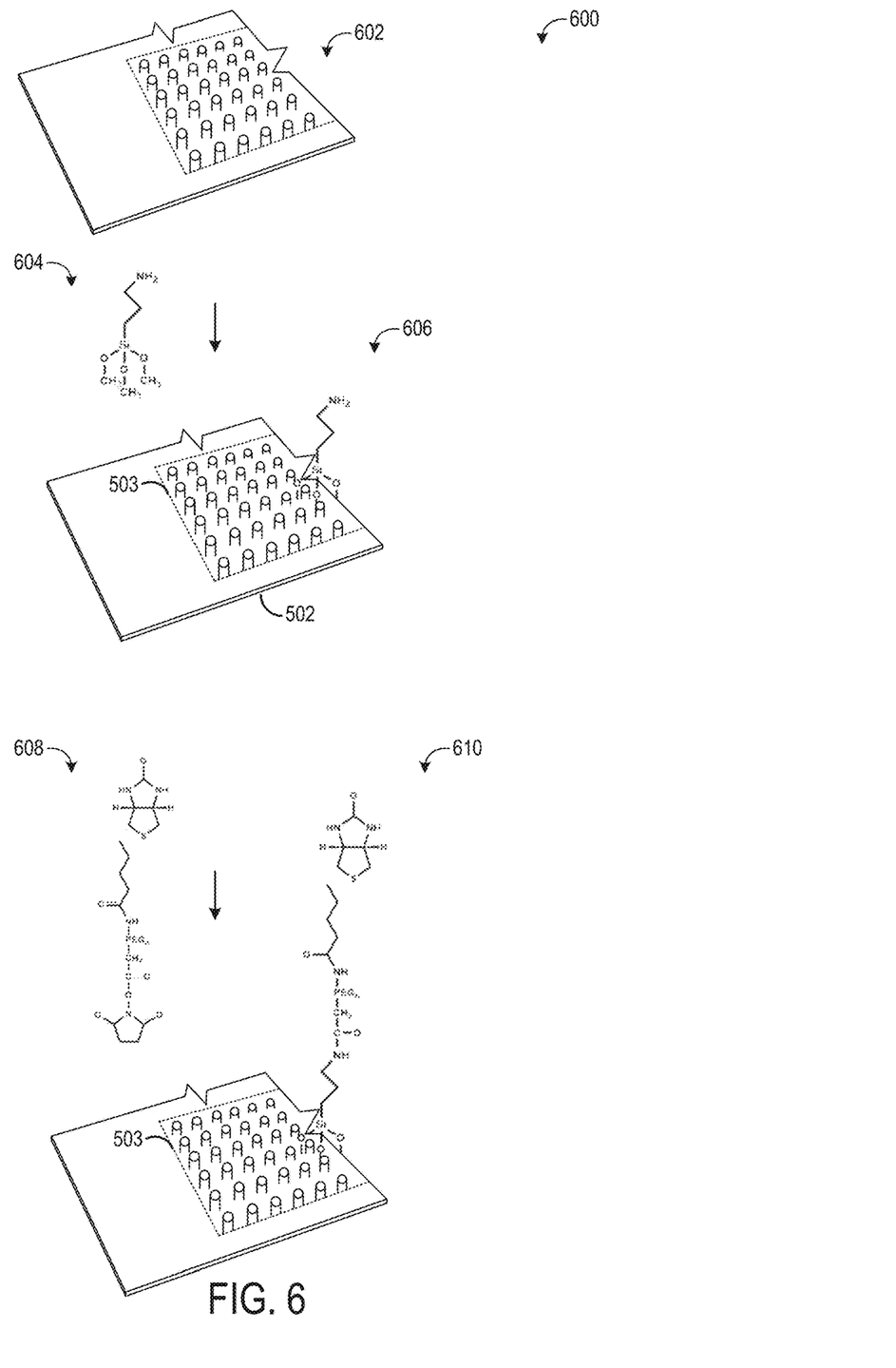
FIG. 6 illustrates an example process for adding biotin groups to a cell-capturing region of a CTCCM chip.
Figure 7:
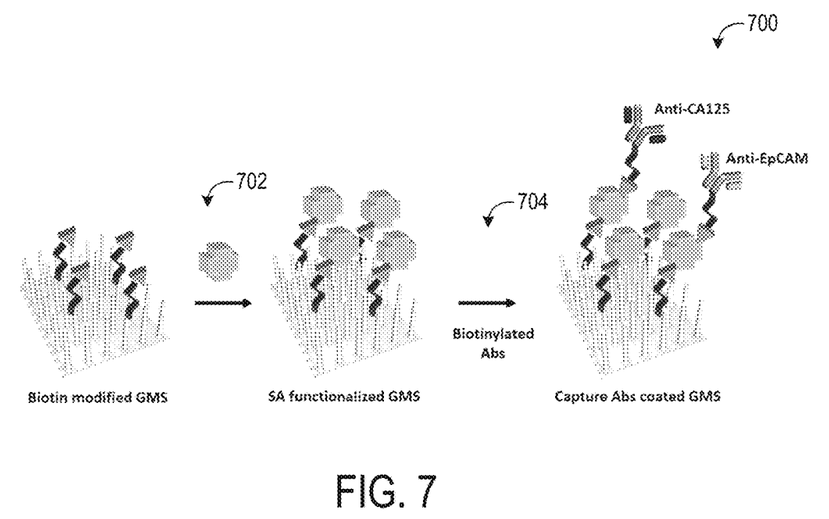
FIG. 7 illustrates an example process for adding antibodies to a cell-capturing region of a CTCCM chip.

To make the surface of the bottom slide of the CTCCM chip function with specific bio-affinity to enrich target cells, two procedures may be completed as illustrated in FIGS. 6 and 7. Firstly, the cell-capturing structures of the glass slide are functionalized with biotin using (3-Aminopropyl) triethoxysilane (APTES). As shown in the process 600 of FIG. 6, APTES 604 is applied to a glass micropillar surface 602 (e.g., the cell-capturing structures/etched surfaces of the glass slide), forming a functionalized surface 606. NHS-PEG-biotin 608 is applied to the functionalized surface 606, causing biotin to be coupled to the amine group via the reactive N-hydroxysuccinimide ester (NHS), forming a biotin labeled surface 610.

After the biotin functional group is modified on the etched surfaces of the bottom slide of the CTCCM chip, through a generally used linker, streptavidin, antibodies may be coupled on the chip for trapping CTCs. The antibodies may be based on affinity for particular cells. For example, if CTCs shed from an ovarian tumor are the target cells to be isolated, antibodies specific to ovarian tumor cells may be coupled on the chip. The two antibodies, anti-EpCAM and anti-CA125, have their corresponding antigens expressed specifically on ovarian cancer cells. As shown in the process 700 of in FIG. 7, antibodies are added to the biotin modified glass micropillar slide or surface (GMS) using a streptavidin linker. For example, at 702, streptavidin linkers are coupled to the biotin groups and then at 704, biotinylated antibodies (e.g., anti-EpCAM, anti-CA125) are added via coupling to the streptavidin. In some examples, neutravidin or other linker may be used. Further, while anti-EpCAM and anti-CA125 antibodies are shown in FIG. 7, other antibodies may be used. The antibodies selected may be chosen based on the target cell type (e.g., antibodies may be selected that are specific to antigens expressed on the cell surface of the target cell type) and affinity for the antigens, for example. Table 1 below lists example cancer types and antibody combinations that may be used to target CTCs of the different cancer types. As explained above, a combination of anti-EpCAM and anti-CA125 may be used to target ovarian cancer cells, with anti-EpCAM comprising 70% of the total antibodies coupled to the bottom slide of the CTCCM chip. Lung cancer cells may be targeted using a combination of 75% anti-EpCAM and 25% anti-EGFR, breast cancer cells may be targeted using a combination of 60% anti-EpCAM and 40% Her2, etc.

TABLE 1

Combination of Capturing antibodies for different cancer type

| Cancer type | Capturing antibodies combo | Percentage of anti-EpCAM (%) |
|---|---|---|
| Ovarian cancer | anti-EpCAM, anti-CA125 | 70 |
| Lung cancer | anti-EpCAM, anti-EGFR | 75 |
| Breast cancer | anti-EpCAM, anti-Her2 | 60 |
| Colon cancer | anti-EpCAM, anti-CLDN1 | 75 |
| Gastric cancer | anti-EpCAM, anti-CEA | 45 |
| Kidney cancer | anti-EpCAM, anti-CA9 | 60 |
| Prostate cancer | anti-EpCAM, anti-PSA | 70 |
| Pancreatic cancer | anti-EpCAM, anti-CA19-9 | 80 |
| Liver cancer | anti-EpCAM, anti-Glypican-3 | 65 |

Once the CTCCM chip is functionalized with antibodies, a sample may be passed over the CTCCM chip (e.g., via the microfluidic channels). The sample may be a blood sample that includes red blood cells and white blood cells from the blood supply, as well as a small proportion of CTCs. The CTCs may specifically bind to the antibodies present on the cell-capturing region, in addition to being selectively immobilized via the long residence time in the microfluidic channels and the micropillar structures.

Figure 8:
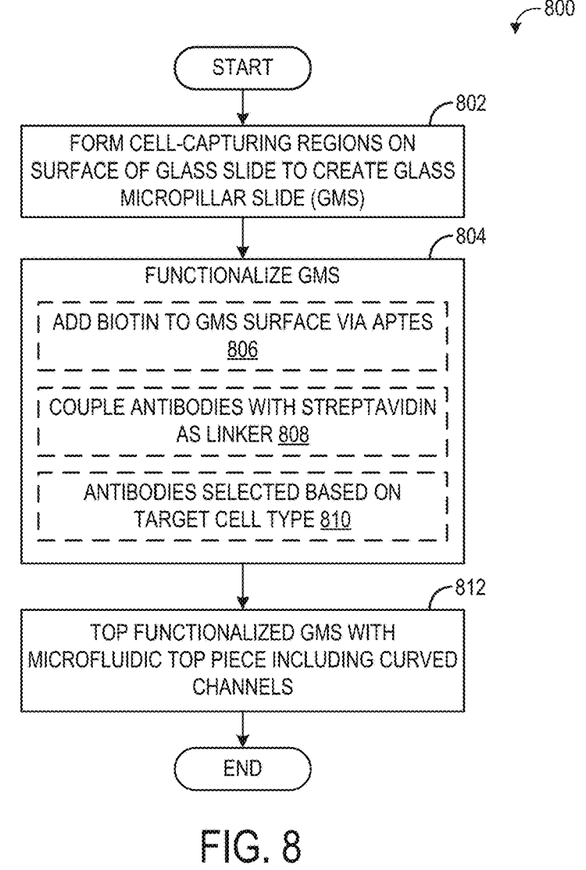
FIG. 8 is a flow chart illustrating an example method for manufacturing a CTCCM chip.

FIG. 8 is a flow chart illustrating a method 800 for manufacturing a CTCCM chip system for use in capturing circulating tumor cells. For example, CTCCM chip 200 of FIG. 2 may be manufactured according to the method 800 shown in FIG. 8. At 802, one or more cell-capturing regions are formed on a top surface of a substrate (e.g., glass slide) to create a glass micropillar slide (GMS). Each cell-capturing region may have a shape of a repeating pattern of two partial circles reversed relative to each other in order to form a switchback or serpentine shaped region, such as the regions 104 shown in FIG. 1 and described above. The glass slide may be etched to form the curved cell-capturing regions. In this manner, the cell-capturing regions may be defined by the presence of the micropillar structures. The substrate may include a suitable number of cell-capturing regions, such as four or eight cell-capturing regions, each having a suitable number of curved portions, such as 11 top curved portions and 10 bottom curved portions.

At 804, the GMS is functionalized. Functionalizing the GMS may include, as indicated at 806, adding biotin to the GMS surface via APTES. For example, the silica in the glass may bond with the APTES molecules and/or the APTES molecules may bond with one another to form a layer of APTES on the GMS surface. As explained above with respect to FIG. 6, biotin may be added to the GMS via NHS-PEG-biotin. Functionalizing the GMS may further include, as indicated at 808, coupling antibodies to the biotin using streptavidin as a linker. For example, antibodies may be prepared with neutravidin or streptavidin as a linker and the antibodies may be supplied to the surface of the GMS, where the neutravidin or streptavidin may bind to the biotin. As indicated at 810, the antibodies may be selected based on the target cell type. For example, when the target cell type that is to be immobilized is ovarian cancer cells, the antibodies that are selected may include anti-EpCAM and anti-CA125.

At 812, the functionalized GMS is topped with a microfluidic top piece, such as the top piece 108 of FIG. 2, to thereby form the CTCCM chip. The top piece includes curved microfluidic channels that correspond to the curved cell-capturing regions of the bottom slide/GMS. The top piece also includes an inlet, an outlet, and suitable coupling mechanisms (e.g., inlet manifold and outlet manifold) to couple the inlet and outlet to the enclosed microfluidic channels that are formed with the top piece is coupled on the GMS. Method 800 then ends.

Thus, method 800 provides for the manufacture of a functionalized CTCCM chip that may be used to selectively isolate tumor cells circulating in a patient blood supply. The functionalized CTCCM chip may include curved microfluidic channels though which a blood sample may be flowed. The curved microfluidic channels may increase a retention time of the circulating tumor cells relative to the blood cells, due to the tumor cells of a relatively large size compared to the red and/or white blood cells. The functionalized CTCCM chip further includes micropillar structures at the cell-capturing regions that are configured to selectively trap the larger CTCs. For example, the bottom glass slide of the CTCCM chip may be etched to form an array of micropillar structures that are sized to trap the CTCs (e.g., micropillar structures having a diameter of 1 μm and height of 0.5 μm). The CTCCM chip may be functionalized to include biotin groups coupled to the top surface of the bottom slide (also referred to as the glass micropillar slide (GMS)). The addition of the biotin allows for antibodies to be coupled to the GMS prior to the blood sample being supplied to the CTCCM chip. The antibodies may be specific to antigens present on the surface of the target cells, thereby further enhancing the isolation of the circulating tumor cells from the patient blood sample.

While method 800 was described above as including the addition of the antibodies prior to the topping of the CTCCM chip with the top piece, in some examples, the top piece may be added to the CTCCM chip before the antibodies are coupled to the biotin groups on the GMS. For example, the antibodies may be present in a solution that is directed through the enclosed microfluidic channels before the patient blood sample is flowed through the channels. In this way, a relatively complete and stable CTCCM chip may be produced, and the more sensitive antibodies may be added at the time of the sample testing.

Thus, FIG. 8 illustrates a method for manufacturing a circulating tumor cell capture microfluidic (CTCCM) chip usable for non-invasive liquid biopsy. In one example, the method includes etching one or more curved cell-capturing regions on a top surface of a glass slide, the etching forming a micropillar structure array, and placing a bottom surface of a top piece in face-sharing contact with the top surface, the bottom surface including one or more corresponding curved microfluidic channels.

Figure 9:
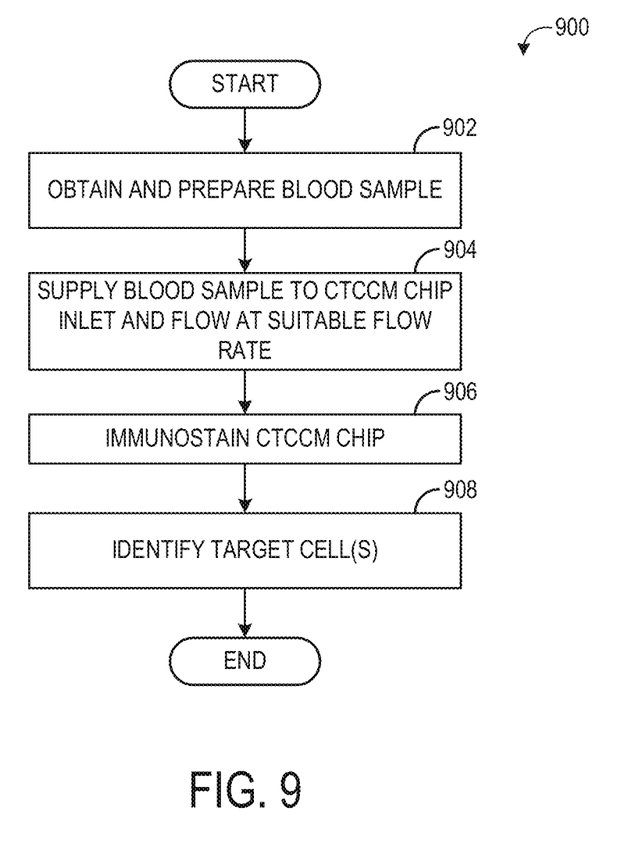
FIG. 9 is a flow chart illustrating an example method for performing circulating tumor cell capture using a CTCCM chip.
Figure 10:
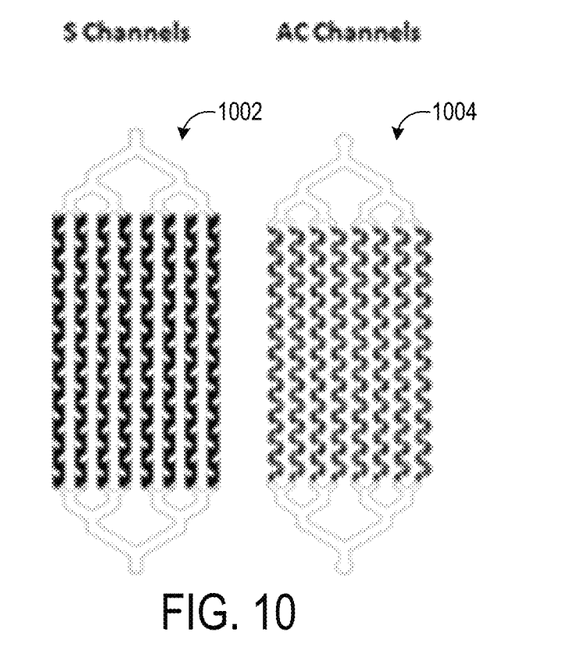
FIGS. 10 and 11 schematically show example straight and curved microfluidic channels.
Figure 11:
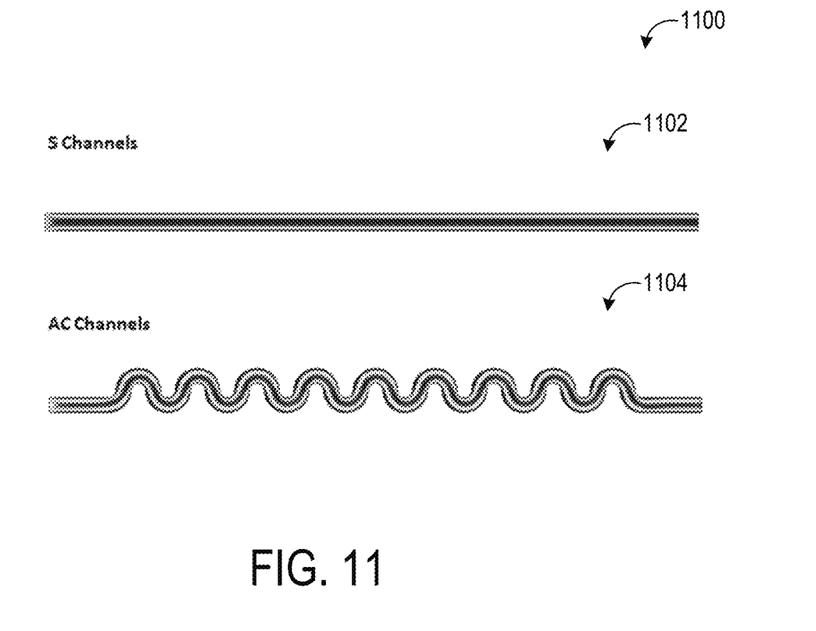
Figure 12:
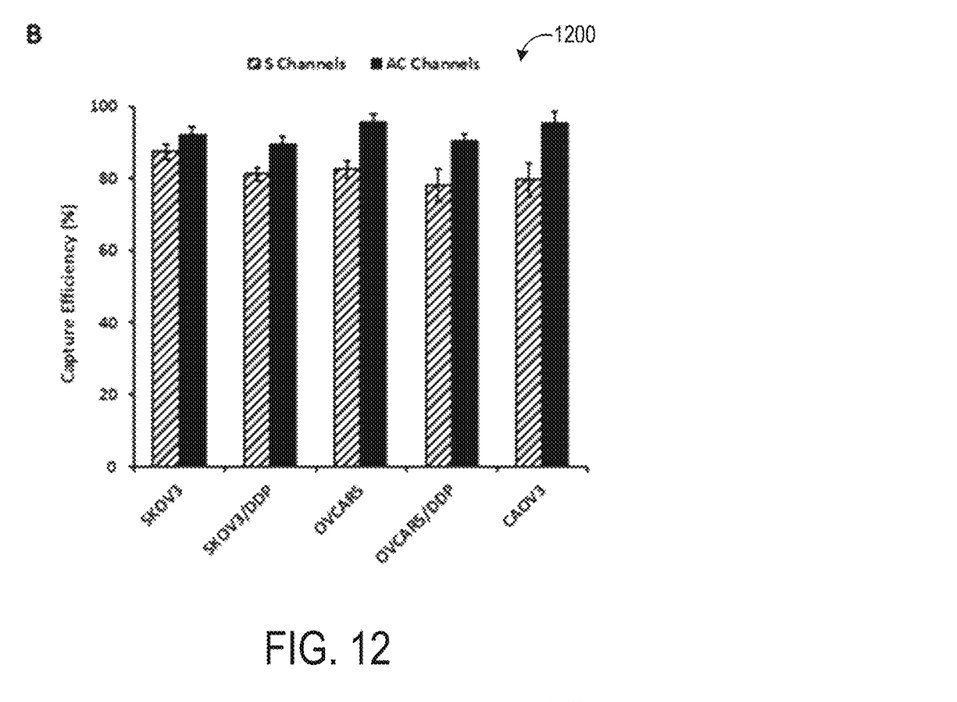
FIGS. 12 and 13 are graphs illustrating cell capture efficiency and purity, respectively, for CTCCM chips including straight and curved microfluidic channels.
Figure 13:
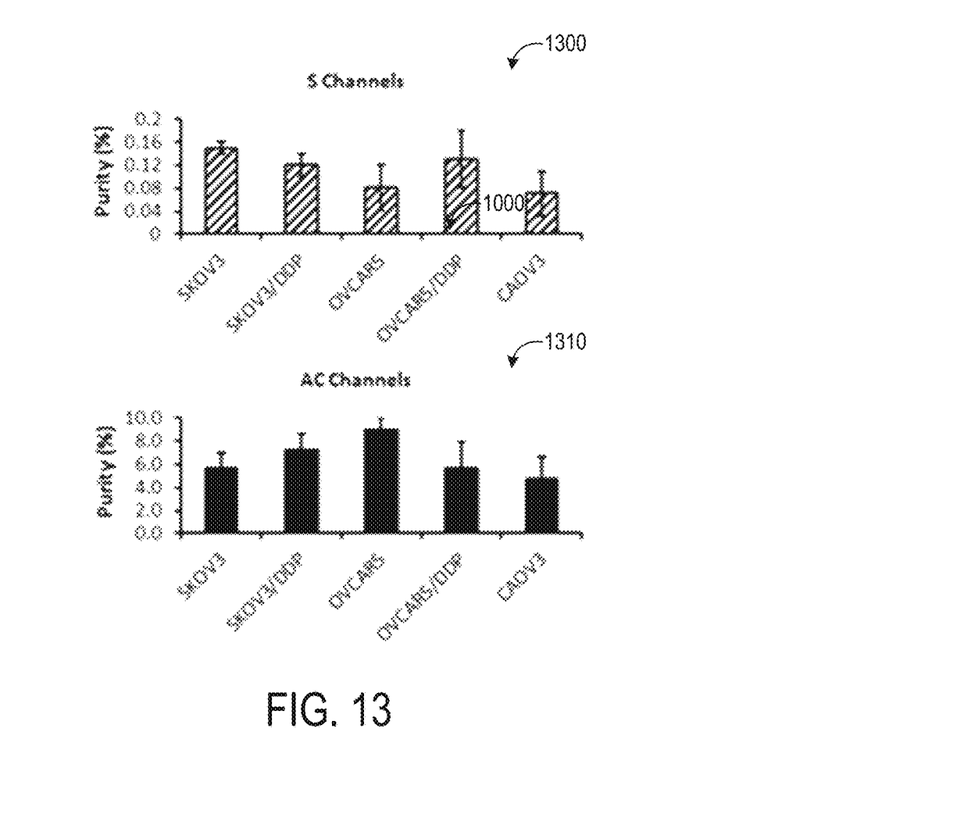

FIG. 9 is a flow chart illustrating a method 900 for capturing circulating tumor cells using a CTCCM chip system, such as the CTCCM chip system described above with respect to FIGS. 1-8. At 902, a blood sample is obtained and prepared for testing. The blood sample may be a patient blood sample obtained from patient that has been diagnosed with or suspected of having cancer, for example. The blood sample may be prepared using standard PBMC isolation protocols, for example. At 904, the prepared blood sample is supplied to the inlet of the CTCCM chip system and is flowed through the enclosed microfluidic channels of the CTCCM chip system. The prepared sample may be flowed at a suitable flow rate, such as a rate between 0.1 and 2 mL/hour. The selected flow rate may balance efficiency (e.g., speed) and cell viability, and as the flow rate increases, cell viability decreases. In one example, the flow rate may be 0.5 mL/hour, which may provide a relatively high efficiency without compromising cell viability.

At 906, the CTCCM chip is immunostained with a selected set of markers that may help visualize the immobilized cells while differentiating the target CTCs from blood cells. For example, the CTCCM chip may be immunostained with DAPI and fluorophore-labeled antibodies against CK and CD45, and further against tumor-specific antibodies such as HE4 (to diagnose early stage ovarian cancer) and/or ERCC (to diagnose ovarian cells that may have developed chemo-resistance). CTCs may have a signature of DAPI+/CK+/CD45−, which may assist in differentiating the CTCs from red blood cells (which will be DAPI−) and white blood cells (which will be CD45+). Early stage ovarian cancer may be detected if the cells are HE4+ while chemo-resistance of ovarian cancer cells may be detected if the cells are ERCC+. Immunostaining may be carried out according to standard immunostaining protocols.

At 908, a target CTC is identified. The target CTC may be identified by placing the immunostained CTCCM chip under a fluorescent microscope and exciting the fluorophores using the appropriate channels of the fluorescent microscope. As explained above, a target CTC may be identified based on the fluorescent signature of the cell matching an expected signature, such as the target CTC being identified based on the cell having a fluorescent signature of DAPI+/CK+/CD45−, and in some examples, additionally having a fluorescent signature that indicates the immobilized cell is from a particular tumor type and/or expresses other features specific to the tumor type. Further, in some examples, the target cell may be additionally or alternatively identified based on cell size. For example, CTCs may have an average diameter of 16.5 and cells that have a size of between 13 and 23 μm may be identified as CTCs, in contrast to white blood cells, which may have an average diameter of approximately 6 μm.

Once a target cell is identified, various tests may be performed, if desired or indicated. In some examples, laser microdissection may be performed to isolate the target cell for further pathological or molecular analysis. Method 900 then ends.

Thus, the methods and systems described herein provide for a CTCCM chip that includes a substrate, such as a glass slide, that includes one or more cell-capturing regions. The cell-capturing regions each include an array of micropillar structures configured to selectively trap CTCs. The cell-capturing regions may extend along a length, width, and height of microfluidic channel(s) that will be formed once a microfluidic top piece is placed on the substrate. The micropillar structure array and microfluidic asymmetric curved structure (repeating curved portions) are configured for physically enriching CTCs. The capture performance may be varied by using different microfluidic channel designs. FIGS. 10-13 illustrate straight and curved channels and the results of a comparison of the "Straight Channels" (S Channels) configuration 1002 with the "Asymmetric Curved Channels" (AC Channels) configuration 1004, as described herein. The performances of these two configurations were evaluated from a point of view of theoretical simulation and also experimental performance on artificial samples. As illustrated by diagram 1100 of FIG. 11, the flow dynamic in different microfluidic channel configurations are simulated, for the straight channels 1102 and the curved channels 1104. Based on the micro-centrifuge force generated in the asymmetric curved channel, CTCs with relative big size with enter low flow rate area giving longer retention time than blood cells with small size in microfluidic channel. Thus, the asymmetric curved channel will retain CTCs in microfluidic channel and dramatically increase the chance to immobilize CTCs on the micropillar glass substrate. Compared to asymmetric curved channels, straight channels cannot actively push CTCs into low flow rate area, which leads to less chance of CTCs being retained in the channel to be captured on the micropillar glass slides.

Additionally, artificial samples prepared by spiking ovarian cancer cell line cells in WBCs (e.g., 500 cancer cells in two million blood cells) were employed to test the capture performance of these two configurations. As indicated by graph 1200 of FIG. 12 and graphs 1300 and 1310 of FIG. 13, the asymmetric curved channel configuration shows higher capture efficiency and also target cell purity after enrichment.

To evaluate CTC capture performance using the CTCCM chip described herein, OVCR5 cells of differing number were spiked in the 2M WBCs in 200 μL PBS solution to be used as artificial samples for the optimization experiment. And standard immunostaining protocol based on CK+/CD45−/DAPI+ was used to count captured CTC number to show the capture efficiency. The results are shown in FIGS. 14-19.

Figure 14:
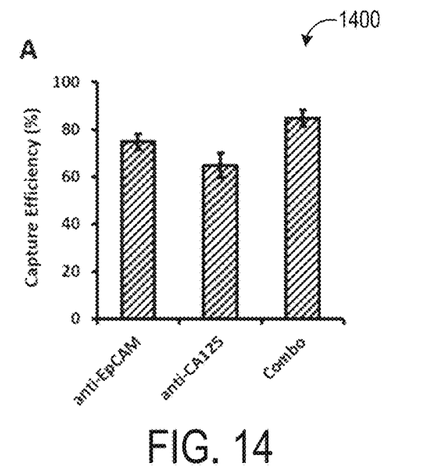
FIGS. 14-19 are graphs illustrating the effects of various CTCCM chip configurations on cell capture efficiency.
Figure 15:
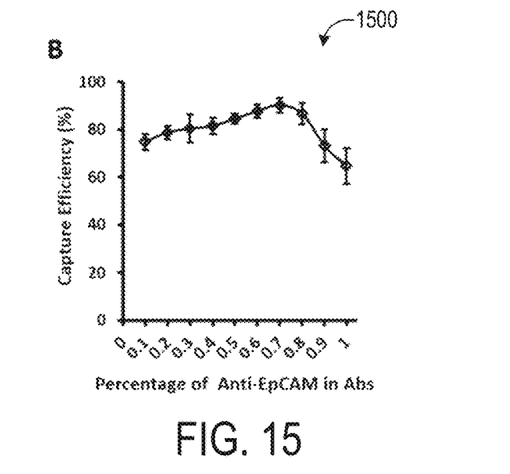
Figure 16:
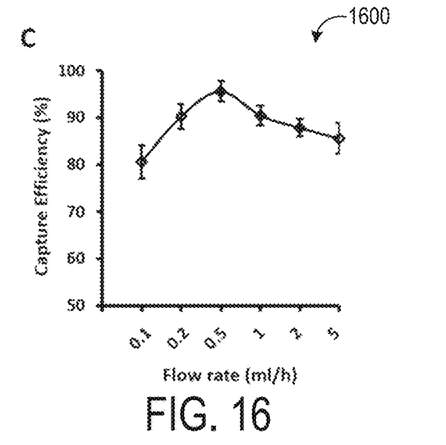
Figure 17:
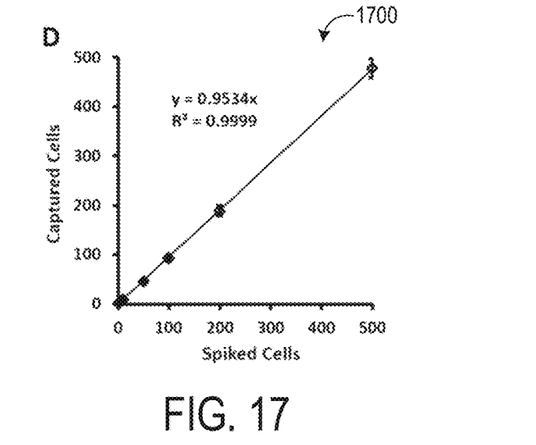
Figure 18:
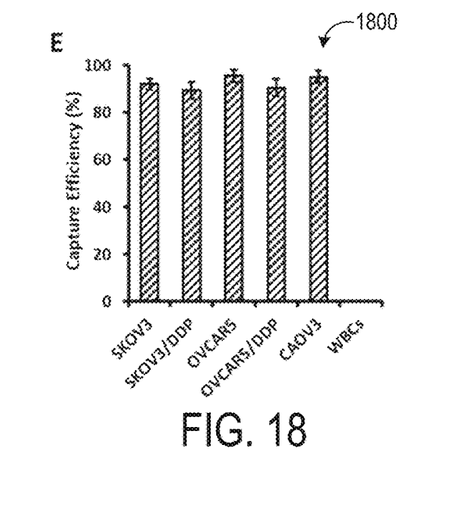
Figure 19:
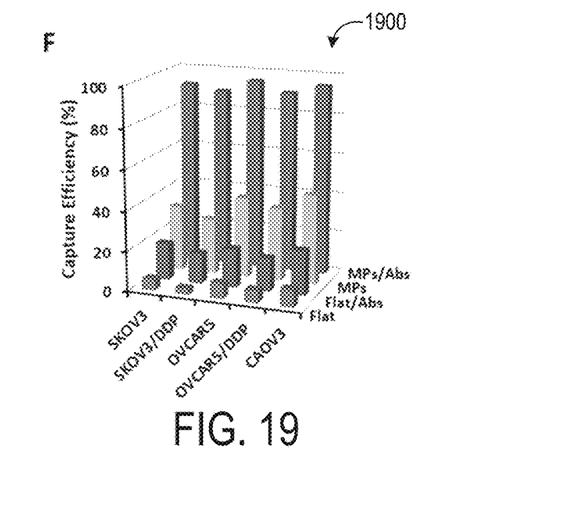

Graph 1400 of FIG. 14(A) illustrates the performance for OVCR5 cell line cells using dual capture agents and capture antibodies separately are compared. The combination of Anti-EpCAM and Anti-CA125 (mixing ratio of 1:1) shows best capture efficiency. Graph 1500 of FIG. 15(B) illustrates the mixing ratio of Anti-EpCAM and Anti-CA125 in their combination is investigated in detail, showing the ratio of 0.7 is the optimal condition. Graph 1600 of FIG. 16(C) illustrates that different flow rates were test for the best performance to capture cancer cells, with a flow rate of 0.5 ml/h having the highest capture efficiency. Graph 1700 of FIG. 17(D) shows that a series of different numbers of OVCR5 were spiked in 2M WBCs as artificial samples, and the sensitivity and calibration curve of the presented method are tested. As shown in FIG. 17, as the number of OVCR5 cells are increased, the capture efficiency is increased. Graph 1800 of FIG. 18(E) shows three ovarian cell lines (SKOV3, OVCAR5, and CAOV3) and two cisplatin-resistant cell lines (SKOV3/DDP and OVCAR5/DDP) tested for capture efficiency, each displaying significantly higher capture efficiency than control WBCs only. Graph 1900 of FIG. 19(F) shows capture efficiency for the five cell lines described above using CTCCM chips having different surface properties. The inclusion of the micropillar structure arrays (MP) increased capture efficiency relative to flat (non-etched or -patterned surfaces), and the inclusion of targeted antibodies further increased capture efficiency.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed The subject matter of the present disclosure includes all novel and non-obvious combinations and sub-combinations of the various processes, systems and configurations, and other features, functions, acts, and/or properties disclosed herein, as well as any and all equivalents thereof.

What is claimed is:

1. A system for capturing circulating tumor cells, comprising:
a substrate having a cell-capturing region, the cell-capturing region having a curved shape and including an array of micropillar structures within the curved shape, wherein the substrate comprises a glass slide, wherein the cell-capturing region is formed on a top surface of the glass slide to create a glass micropillar slide (GMS), wherein the glass slide is etched to form the curved cell-capturing region, wherein the GMS is functionalized by adding biotin to a surface of the GMS by using (3-Aminopropyl) triethoxysilane (APTES), wherein the biotin is added to the GMS via NHS-PEG-biotin, wherein the cell-capturing region is a first cell-capturing region, and wherein the substrate has a plurality of additional cell-capturing regions arranged in parallel, each additional cell-capturing region including an array of micropillar structures and having the curved shape.

2. The system of claim 1, wherein the array of micropillar structures are formed on a top surface of the substrate within the cell-capturing region.

3. The system of claim 1, wherein each micropillar structure has a diameter in a range of 0.8-1.2 μm.

4. The system of claim 1, wherein each micropillar structure has a height in a range of 0.2-2 μm.

5. The system of claim 1, wherein each micropillar structure is spaced apart from neighboring micropillar structures by an equal amount.

6. The system of claim 1, further comprising a top piece including a plurality of curved microfluidic channels, each curved microfluidic channel having a shape that matches the curved shape of each cell-capturing region.

7. The system of claim 1, wherein the cell-capturing region includes biotin groups.

8. The system of claim 7, further comprising one or more antibodies having avidin-based linkers, the one or more antibodies configured to bind to the biotin groups via the avidin-based linkers.

9. A system for capturing circulating tumor cells (CTCs), comprising: a substrate including a plurality of curved, parallel cell-capturing regions formed on a top surface of the substrate, each cell-capturing region including an array of micropillar structures; a top piece including a plurality of curved, parallel microfluidic channels located on a bottom surface of the top piece, each microfluidic channel having a shape that matches a shape of a corresponding cell-capturing region; and one or more antibodies binds to at least one cell-capturing region of the plurality of cell-capturing regions via a linker, wherein the substrate comprises a glass slide, wherein the cell-capturing region is formed on a top surface of the glass slide to create a glass micropillar slide (GMS), wherein the glass slide is etched to form the curved cell-capturing region, wherein the GMS is functionalized by adding biotin to a surface of the GMS by using (3-Aminopropyl) triethoxysilane (APTES), wherein the biotin is added to the GMS via NETS-PEG-biotin.

10. The system of claim 9, wherein when the bottom surface of the top piece is in face-sharing contact with the top surface of the substrate, a respective microfluidic channel and corresponding cell-capturing region form a respective enclosed curved microfluidic channel enables a sample to flow.

11. The system of claim 9, wherein the top piece is comprised of a silicone material.

\* \* \* \* \*